United States Patent [19]

McPhee

[11] Patent Number: 5,429,607

[45] Date of Patent: Jul. 4, 1995

[54] ELASTOMERIC SYRINGE ACTUATION DEVICE

[75] Inventor: Charles J. McPhee, Huntington Beach, Calif.

[73] Assignee: I-Flow Corporation, Calif.

[21] Appl. No.: 208,729

[22] Filed: Mar. 9, 1994

[51] Int. Cl.[6] ............................................. A61M 5/148
[52] U.S. Cl. ................................. 604/131; 604/156
[58] Field of Search ............... 604/156, 130, 131, 132, 604/133, 134

[56] References Cited

U.S. PATENT DOCUMENTS

| | | | |
|---|---|---|---|
| 2,626,604 | 1/1953 | Napeau | 604/156 |
| 2,995,373 | 8/1961 | Cox | 604/130 |
| 3,051,173 | 8/1962 | Johnson et al. | 604/156 |
| 4,381,006 | 4/1983 | Genese | 128/218 |
| 4,597,754 | 7/1986 | Thill et al. | 604/154 |
| 4,636,197 | 1/1987 | Chu | 604/131 |
| 4,755,172 | 7/1988 | Baldwin | 604/131 |
| 4,950,163 | 8/1990 | Zimble | 433/215 |
| 4,966,585 | 10/1990 | Gangemi | 604/131 |
| 5,024,662 | 6/1991 | Menes et al. | 604/131 |
| 5,078,679 | 1/1992 | Reese | 604/121 |
| 5,100,389 | 3/1992 | Vaillancourt | 604/135 |
| 5,176,643 | 1/1993 | Kramer et al. | 604/135 |
| 5,312,354 | 8/1994 | Allan et al. | 605/156 |

FOREIGN PATENT DOCUMENTS

| | | |
|---|---|---|
| 69428 | 9/1968 | German Dem. Rep. |
| 220582A1 | 1/1984 | German Dem. Rep. |
| 2142827 | 1/1985 | United Kingdom ........ 604/131 |

*Primary Examiner*—Paul J. Hirsch
*Attorney, Agent, or Firm*—Klein & Szekeres

[57] ABSTRACT

An elastomerically-actuated syringe actuation device comprises a grommet that fits around the outlet tip of a syringe; an end cap, having a finger grip, that engages the distal end of the plunger of the syringe; and an elastomeric element that connects the grommet and the end cap. When the grommet is seated around the outlet tip, and the end cap is engaged against the distal end of the plunger with the plunger in its withdrawn position, the elastomeric element is stretched along the syringe, between the grommet and the end cap, thereby biasing the plunger toward its inserted position. As the elastomeric element restores itself to its unstretched configuration, it provides a driving force against the plunger to push the plunger into the barrel of the syringe, thereby expressing the fluid contained in the barrel out of the outlet tip. In one embodiment, the elastomeric element is an elastic strap having first and second ends removably secured to the grommet so as to be length-adjustable, and an intermediate portion secured to the end cap. In a second embodiment, the elastomeric element is a continuous elastic band removably secured to both the grommet and the end cap. In both embodiments, the elastomeric element is secured to the end cap so that it is spaced away from the barrel of the syringe.

41 Claims, 3 Drawing Sheets

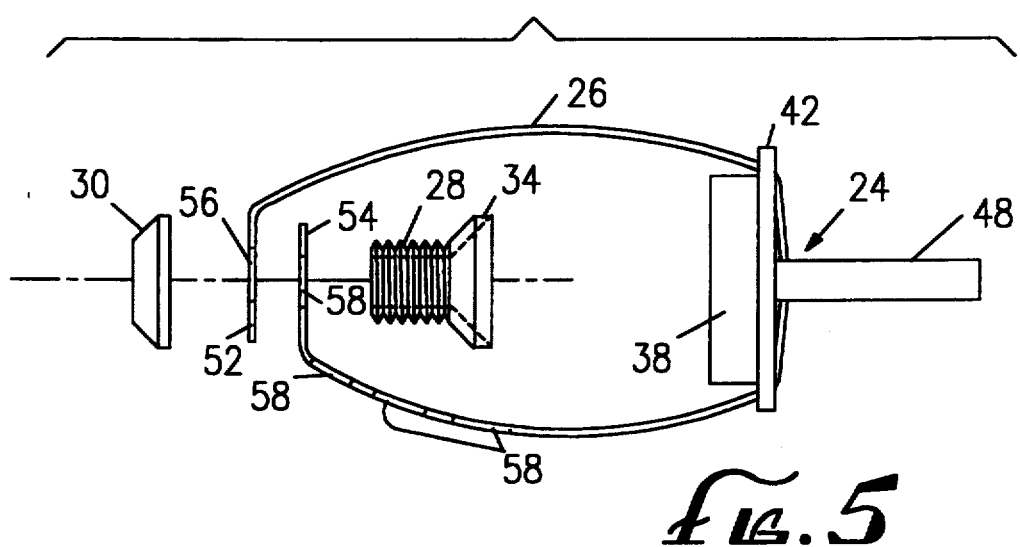
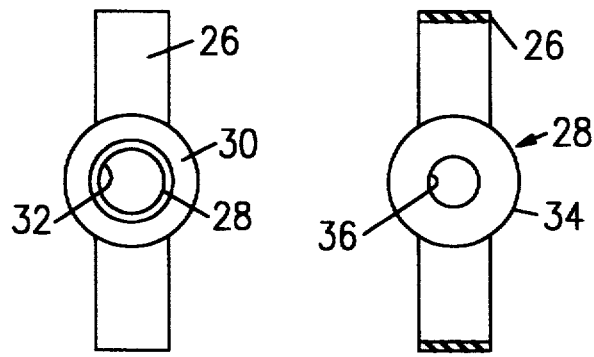 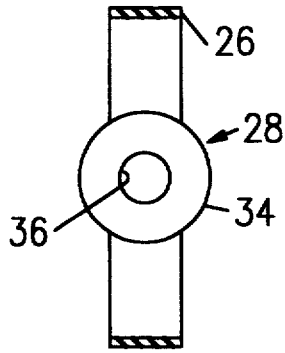

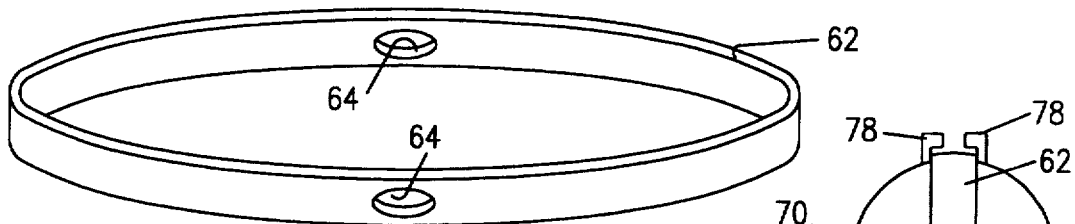
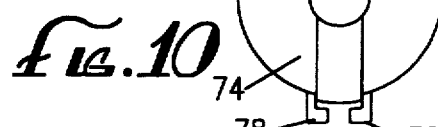
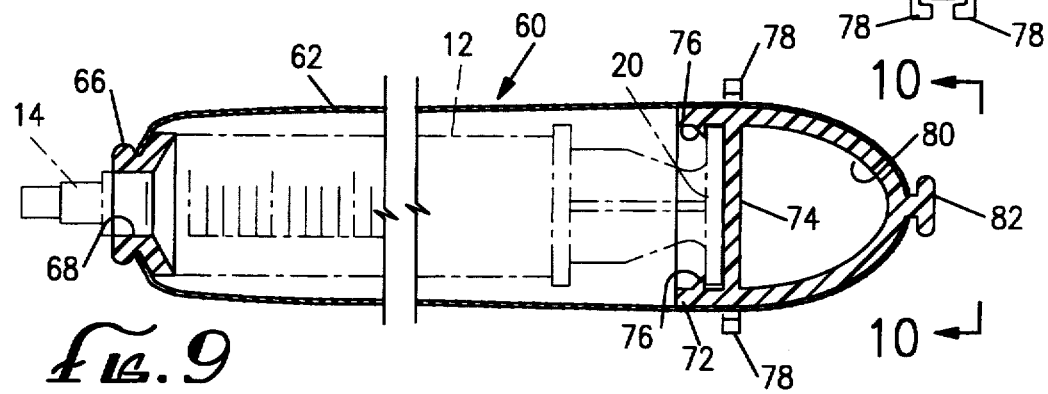
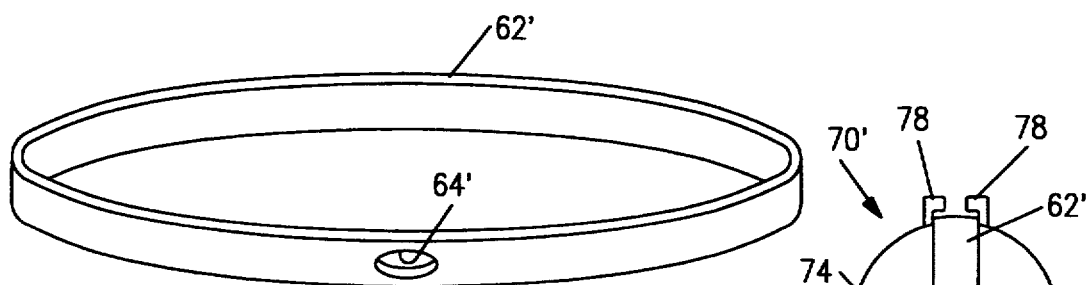
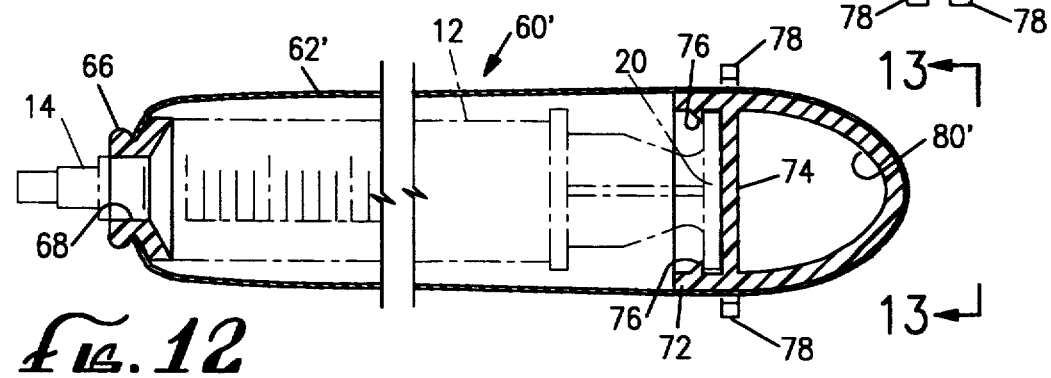

ELASTOMERIC SYRINGE ACTUATION DEVICE

BACKGROUND OF THE INVENTION

This invention relates generally to the field of fluid infusion devices for medical applications, More specifically, it relates to infusion devices used for the administration of a liquid medicament to a patient from a filled syringe into an intravenous (IV) administration system.

Various devices have been developed for the intravenous (IV) infusion of liquid medicaments into a patient at a controlled flow rate over an extended period of time. For example, gravity flow IV administration sets have been employed for many years, and more recently, IV administration sets with electrically powered pumps have been developed.

There are applications in which a more compact and inexpensive type of infusion device is desired or required. For example, in addition to direct infusion from a syringe, it is frequently necessary to infuse a secondary fluid into a primary IV flow from a gravity flow or electrically-pumped IV administration set. Also, infusion into an ambulatory patient frequently requires an infusion device that is less bulky, less complex, and easier to use than gravity flow or pump-powered devices. For such applications, relatively complex self-powered infusion devices are frequently used.

With a typical, manually actuated IV administration syringe, infusion over an extended period of time is usually impractical or inconvenient, and achieving a substantially constant flow rate throughout the infusion is often difficult. To overcome these problems, the prior art has devised a variety of mechanisms for actuating the syringe so as to achieve a more or less constant fluid flow over an extended period of time. One type of syringe actuation mechanism is that which utilizes either internal or external springs to displace the plunger of the syringe. Examples of such mechanisms are shown in the following U.S. Pat. Nos. 4,381,006 - Genese; 4,597,754 - Thill et al.; 4,608,042 - Vanderveen et al.; 4,623,330 - Laby et al.; 4,755,172 - Baldwin; 4,966,585 - Gangemi; 5,078,679 - Reese; and 5,100,389 Vaillancourt.

While the spring-powered mechanisms of the prior art overcome, to varying degrees, the above-mentioned problems associated with manual syringes, they suffer from other shortcomings, such as complexity, relatively heavy weight, and relatively high costs. Those with spring mechanisms inside the syringe necessitate increased costs in the manufacture of the syringe itself, making such mechanisms inappropriate for single use, disposable syringes. Those employing a spring mechanism external to the syringe are typically cumbersome to use, often necessitating the extra step of installing the syringe in a dispenser.

Another approach has been to use elastomeric bands to provide the plunger-depressing force in a syringe. Examples of such devices are shown in U.S. Pat. No. 4,636,197 - Chu; U.S. Pat. No. 4,950,163 - Zimble; U.S. Pat. No. 5,024,662 - Menes et al.; and German Democratic Republic (GDR) Pat. No. 69,428. The elastomerically powered syringes are typically simpler and less costly to manufacture than the spring actuated devices discussed above. They are also usually easier and more convenient to use, and they are more readily adaptable for single use applications. A principal drawback to these prior art elastomerically powered devices, however, is that they require specially designed syringes, and they are thus not readily adapted for use with standard IV administration syringes.

Therefore, there has been an unfulfilled need for a compact, self-actuated IV administration device that provides a nearly constant flow rate over an extended period of time, while also being economical to manufacture, easy and convenient to use, and adaptable for single use applications with the standard IV administration syringe.

SUMMARY OF THE INVENTION

Broadly, the present invention is an elastomerically-actuated syringe actuation device, comprising a grommet assembly that fits over the outlet tip of an IV administration syringe; an end cap, having a handle or finger grip, that engages the distal end of the plunger of the syringe; and an elastomeric element that connects the grommet assembly and the end cap, so that when the grommet assembly is seated around the outlet tip, and the end cap is seated on the distal end of the plunger, the elastomeric element extends longitudinally along diametrically opposite sides of the syringe, between the grommet assembly and the end cap. When the device is installed on a previously-filled syringe having its plunger pulled out of the syringe barrel to its withdrawn position, the elastomeric element is stretched, placing it under tension, so that it biases the plunger toward its inserted position. As the elastomeric element restores itself to its unstretched configuration, it provides a driving force against the plunger to push the plunger into the barrel of the syringe, thereby expressing the fluid contained in the barrel out of the outlet tip.

In one specific preferred embodiment, the elastomeric element is an elongate elastic strap, having a single hole near one end, and a plurality of holes in a linear array near the other end. The grommet assembly comprises an externally-threaded, hollow, cylindrical, bolt-like attachment fitting that fits through the single hole in the one end of the strap, and, with the strap ends overlapping, through one of the plurality of holes near the other end. An internally-threaded annular collar is removably threaded onto the end of the fitting that extends through the strap ends to removably lock the ends of the strap to the grommet assembly.

The end cap comprises a short, hollow, cylindrical sleeve with a closed distal end wall that includes an annular peripheral flange. The hollow interior of the sleeve is dimensioned to receive the circular thumb rest of the plunger, and the interior wall surface of the sleeve is provided with latch means for releasably grasping the thumb rest. Extending distally from the exterior surface of the distal end wall of the end cap is a ring-shaped handle or finger grip, having a large central orifice. Two diametrically opposed slots are provided in the annular flange to accommodate the elastic strap.

The strap extends longitudinally from the grommet assembly to the end cap, passing through one slot in the end cap flange, from the proximal side of the flange to the distal side thereof. The strap then extends laterally across the exterior surface of the distal end wall of the end cap, through the orifice of the finger grip, to the other slot, through which it passes back to the proximal side of the flange. From there, the strap extends longitudinally back to the grommet assembly.

The device is used by installing it on a filled infusion syringe having its plunger in the withdrawn position, and having outflow from its outlet tip obstructed by any suitable, conventional closure of the outlet tip, or by a conventional clamp applied to a catheter or conduit attached to the outlet tip. The grommet assembly is attached to the strap by inserting the externally-threaded fitting through the single hole in the one end of the strap, and through a selected one of the plurality of holes in the other end, the selection being based on the size of the syringe on which the device is to be installed. The strap is locked to the grommet assembly by threading the annular, internally-threaded collar onto the fitting. The grommet assembly is then seated around the outlet tip of the syringe, and the strap is stretched until the thumb rest of the plunger is received in the end cap of the device, thereby placing the strap under tension and biasing the plunger toward its inserted position in the syringe barrel. With outflow from the syringe being obstructed, however, inward movement of the plunger from its withdrawn position to its inserted position is prevented.

When it is desired to discharge the contents of the syringe, the outflow obstruction means are removed. The potential energy represented by the elastomeric tension in the strap is then released, generating a linearly-directed driving force against the thumb rest to drive the plunger into the barrel, thereby expressing the contents of the syringe out of the outlet tip. This driving force has a very slow rate of decay over time, so that the flow rate expressed from the syringe remains reasonably close to its nominal level until the syringe is nearly empty.

In another preferred embodiment, the elastomeric element is a continuous elastic band, with a pair of diametrically-opposed holes. Instead of a two-piece grommet assembly, a unitary grommet is placed around the outlet tip and inserted into a first one of the holes in the band. The end cap comprises an arcuate grip portion extending distally from the distal end wall, a pair of diametrically-opposed band guides extending radially outwardly from the end wall, and a knob or button extending distally from the distal end of the grip portion. The band is passed through the band guides and around the exterior surface of the grip portion, with the knob or button being received in the second one of the holes in the band. In a variation of this embodiment, the second band hole and the button or knob are omitted.

From the foregoing, it can be seen that the present invention provides an elastomerically-powered IV administration syringe actuation device that is easy to use, and adaptable for use with standard IV administration syringes in a wide variety of sizes. Moreover, the present invention is simple and inexpensive to manufacture, and thus is readily adaptable to single use (disposable) applications. These and other advantages of the present invention will be more readily understood from the detailed description that follows.

BRIEF DESCRIPTION OF THE DRAWINGS

FIG. 5 is an exploded elevational view of the syringe actuation device, in accordance with the first preferred embodiment of the present invention;

FIG. 6 is an elevational view, taken along line 6—6 of FIG. 3;

FIG. 7 is a cross-sectional view, taken along line 7—7 of FIG. 3;

FIG. 8 is a perspective view of an elastic band configured for use in a second preferred embodiment of the invention;

FIG. 9 is a cross-sectional view, similar to that of FIG. 4, showing the second preferred embodiment of the invention installed on a syringe;

FIG. 10 is an elevational view, taken along line 10—10 of FIG. 9;

FIG. 11 is a perspective view of an elastic band configured for use in a modified form of the second preferred embodiment of the invention;

FIG. 12 is a cross-sectional view, similar to that of FIG. 9, showing the modified form of the second preferred embodiment of the invention installed on a syringe; and FIG. 13 is an elevational view, taken along line 13—13 of FIG. 12.

DETAILED DESCRIPTION OF THE PREFERRED EMBODIMENTS

Figure 1:
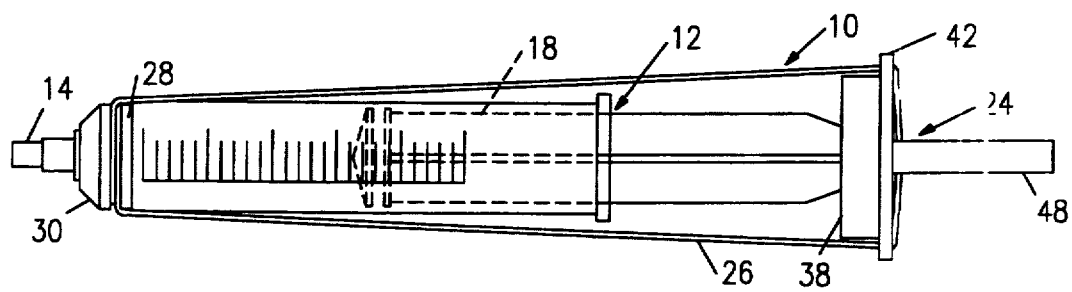
FIG. 1 is a side elevational view of a syringe actuation device, in accordance with a first preferred embodiment of the present invention, showing the device installed on a standard IV administration syringe.
Figure 2:
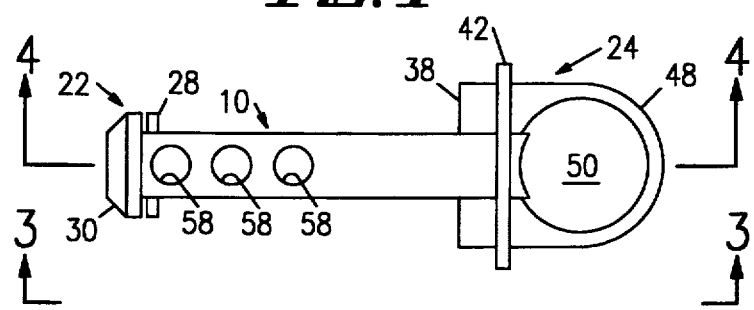
FIG. 2 is a side elevational view of the first preferred embodiment of the syringe actuation device of FIG. 1, the device having been removed from the syringe and rotated 90 degrees around the longitudinal axis of FIG. 1.
Figure 3:
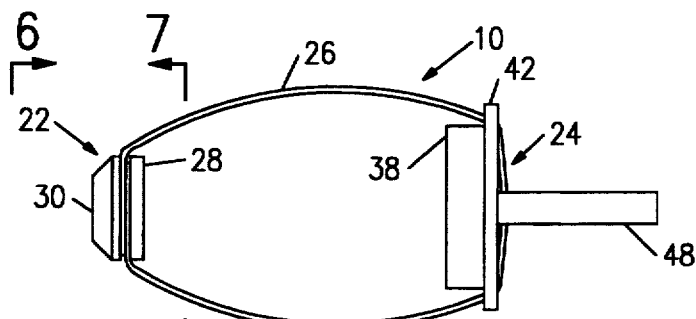
FIG. 3 is an elevational view of the first preferred embodiment of the syringe actuation device, taken along line 3—3 of FIG. 2.

Referring to the drawings, an elastomeric syringe actuation device 10, in accordance with a first preferred embodiment of the present invention, is shown both installed on (FIGS. 1 and 4) and separate from (FIGS. 2, 3, and 5 through 7) a standard IV administration syringe 12. The syringe 12 has an outlet tip 14 at its proximal end, of the standard configuration that accommodates a typical Luer fitting (not shown). Extending distally from the tip 14 is a substantially cylindrical barrel 16, the interior of which provides a reservoir for a liquid therapeutic agent (hereinafter referred to as a "medicament"). A plunger 18 is received within the barrel 16 for longitudinal movement between a withdrawn position (shown in FIGS. 1 and 4) and an inserted position. The plunger 18 has an actuation portion 19 extending distally from the barrel 16, the actuation portion 19 terminating in a flattened, substantially circular thumb rest 20.

The elastomeric syringe actuation device 10 comprises a grommet assembly 22 that fits over and seats around the outlet tip 14 of the syringe 12; an end cap 24 that engages the thumb rest 20 of the syringe plunger 18; and an elastomeric element 26 that connects the grommet assembly 22 and the end cap 24.

As best shown in FIGS. 5 through 7, the grommet assembly 22 comprises an externally-threaded, cylindrical, bolt-like fitting 28 and an internally-threaded annular collar 30 that is removably threaded onto the fitting 28. The fitting 28 has an axial bore 32 and an enlarged-diameter head 34 having a central orifice 36 that communicates with the bore 32.

Figure 4:
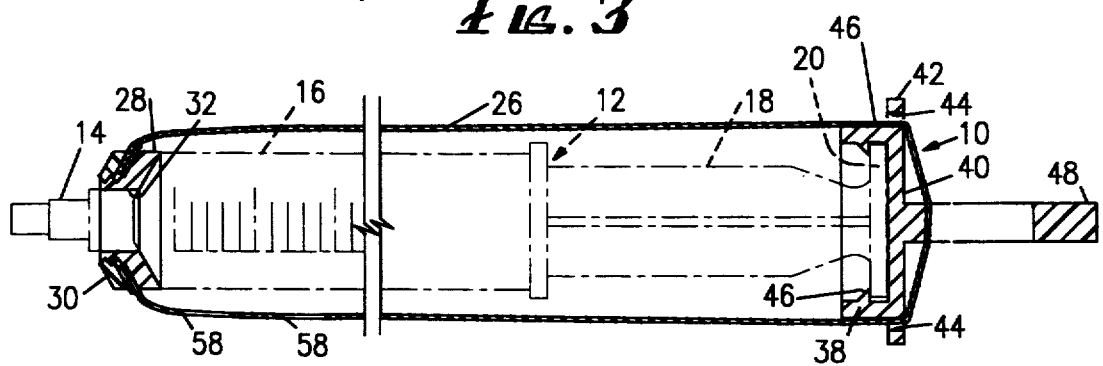
FIG. 4 is a cross-sectional view, taken along line 4—4 of FIG. 3, showing the first preferred embodiment of the syringe actuation device installed in its stretched position on a syringe.

As best shown in FIG. 4, the end cap 24 comprises a short, cylindrical sleeve 38 having an open proximal end, and a closed distal end wall 40 that includes an annular peripheral flange 42. The hollow interior of the sleeve 38 is dimensioned to receive the thumb rest 20, which seats against the interior surface of the end wall 40. The flange 42 is provided with a pair of diametrically-opposed guide slots 44. Extending radially inwardly from the interior wall surface of the sleeve 38 are a pair of diametrically-opposed fingers 46 that provide means for releasably engaging or latching the thumb rest 20. Extending distally from the exterior surface of the distal end wall 40 of the end cap 24 is a ring-shaped handle or finger grip 48, having a large central orifice 50.

In the preferred embodiment, as best shown in FIG. 5, the elastomeric element 26 is an elongate elastic strap having a first end portion 52 and a second end portion 54, with an intermediate portion therebetween. A single hole 56 is formed in the strap 26 near the first end portion 52 and a plurality of holes 58 are formed in a linear array near the second end portion 54. The end cap 24 is attached to the approximate middle of the length of the strap 26 by passing one of the end portions 52, 54 through one of the slots 44 in the end cap flange 42, from the proximal side to the distal side thereof. That one end portion is then extended across the exterior (distal) surface of the distal end wall 40, through the orifice 50 of the finger grip 48, and then through the other slot 44 back to the proximal side of the flange 42. The one end portion of the strap is then pulled through the slots 44 until the end cap 24 is situated approximately mid-way along the length of the strap 26.

The strap end portions 52, 54 are removably attached to the grommet assembly 22 by means of the single hole 56 and a selected one of the plurality of holes 58. Specifically, as best shown in FIG. 5, with the annular collar 30 removed from the fitting 28, the proximal end of the fitting 28 is passed through the single hole 56, and, with the strap end portions 52, 54 overlapping, through one of the plurality of holes 58, selected on the basis of the size of the syringe on which the device 10 is to be installed. The collar 30 is then threaded onto the fitting 28 until the strap end portions 52, 54 are snugly captured between the collar 30 and the head 34 of the fitting 28.

Because the slots 44, through which the strap 26 is passed, are disposed radially outwardly from the syringe barrel 16 by their placement in the flange 42, the slots 44 and the flange 42 provide an "outrigger" effect, whereby the strap 26 is positioned away from the syringe barrel 16, as best shown in FIG. 1. This separation between the strap 26 and the syringe barrel 16 prevents abrasion of the strap 26 against the syringe barrel 16, thereby preventing damage to the strap 26, and allowing for a smoother movement of the syringe plunger 18 when the device 10 is used in the manner described below.

To use the actuation device 10, a syringe 12 is filled with the desired quantity of medicament, and then the outflow from the syringe is obstructed by conventional means, such as a clamp (not shown) on the IV tubing (not shown) connected to the outlet tip 14 of the syringe. With the outflow obstructed, the plunger 18 remains in its withdrawn position, as shown in FIGS. 1 and 4.

The actuation device 10 is then installed on the syringe 12 by seating the grommet assembly 22 around the outlet tip 14, with the tip 14 extending through the central orifice 36 and axial bore 32 of the fitting 28. The end cap 24 is then pulled distally, by means of the finger grip 48, until the thumb rest 20 of the plunger 18 can be seated within the sleeve 38, with the edge of the thumb rest 20 being engaged by the latching fingers 46. In this position, shown in FIGS. 1 and 4, the elastomeric element or strap 26 is stretched so that it is under tension, thereby biasing the plunger 18 toward its inserted position.

When the obstruction to the syringe outflow is removed (e.g., by removing the above-mentioned clamp), the plunger 18 is free to be moved toward its inserted position. This is accomplished by the release of the potential energy stored in the stretched strap 26 as it elastomerically restores itself to its unstretched configuration, thereby generating a linearly-directed force against the thumb rest 20 which drives the plunger 18 in the proximal direction toward its inserted position. The proximal movement of the plunger 18 into the barrel 16 causes the medicament therein to be discharged from the outlet tip 14. The driving force generated by the strap 26 has a very slow rate of decay, so that the flow rate of medicament from the syringe 12 remains reasonably close to a preselected nominal flow rate until the syringe 12 is empty, or nearly so.

A syringe 12 may be filled and stored with the actuation device 10 installed on it as described above (and with the syringe's outflow suitably obstructed). Should the strap 26 break while the syringe 12 is stored (or while it is being used), one or both of the latching fingers 46 in the end cap sleeve 38 is likely to be retained in engagement with the thumb rest 20, thereby keeping the actuation device 10 from "flying" off of the syringe 12 in response to the release of energy when the strap 26 breaks. In addition, the end cap 24 and the grommet assembly 22 are securely (although removably) attached to the strap 26, so that, even if the strap 26 should break, all of the components of the device 10 are held together, with a minimal probability of separation or loss of a component.

A syringe actuation device 60, in accordance with a second preferred embodiment of the invention, is shown in FIGS. 8, 9, and 10. In this second embodiment, the elastomeric element is a continuous elastic band 62, having a pair of diametrically-opposed holes 64. A unitary grommet 66, having a hollow bore 68, is inserted into a first one of the holes 64 to attach the band 62 to the grommet 66. The outlet tip 14 of the syringe 12 is inserted into and through the bore 68, so that the grommet 66 is seated around the outlet tip 14.

An end cap 70 comprises a short cylindrical sleeve 72 having an open proximal end, and a closed distal end wall 74. The hollow interior of the sleeve 72 is dimensioned to receive the thumb rest 20 of the syringe 12, which seats against the interior surface of the end wall 74. Extending radially inwardly from the interior wall surface of the sleeve 72 are a pair of diametrically-opposed fingers 76 that provide means for releasably engaging or latching the thumb rest 20.

The end cap 70 is provided with a pair of diametrically-opposed band guides, each of which comprises a pair of guide fingers 78 extending radially outwardly from the end wall 74, and then angled toward each other substantially at a right angle, with a gap therebetween into which the band 62 can be inserted. The guide fingers 78 position the elastic band 62 so that it is spaced from the syringe barrel, and thus function much like the end cap slots 44 of the first embodiment.

An arcuate grip portion 80 extends distally from the distal end wall 74, and a knob or button 82 extends distally from the distal end of the grip portion 80. The band 62 is passed between the band guide fingers 78 and around the exterior surface of the grip portion 80, with the knob or button 82 being received in the second one of the holes 64 in the band 62 to secure the band 62 to the grip portion 80 of the end cap 70.

A modification of the second embodiment is illustrated in FIGS. 11, 12, and 13. In accordance with this modification, an elastomeric syringe actuation device 60' differs from the embodiment of FIGS. 8, 9, and 10 primarily in having an end cap 70' with a grip portion 80' that has a smooth, uninterrupted exterior surface, without any button or knob. Accordingly, in this modification, the device 60' employs an elastic band 62' that requires only a single hole 64' for the attachment of the band to the grommet 66, in the manner previously described. For being secured to the end cap 70' the band 62' relies on the guide fingers 78 and on frictional contact with the exterior surface of the grip portion 80'.

The second embodiment of FIGS. 8 through 13 is employed in a manner similar to that of the first embodiment of FIGS. 1 through 7. As compared to the first embodiment, the chief advantage of the second is lower cost, although it can accommodate a narrower range of syringe sizes.

From the foregoing description, it can be seen that the present invention provides an elastomerically-powered actuation device for an IV administration syringe that is easy and convenient to use, and that is adaptable to a wide variety of conventional IV administration syringes over a broad range of sizes. In addition, the present invention is simple and inexpensive to manufacture, and is therefore suitable for use as a disposable device. Furthermore, the invention provides a flow rate from the syringe that remains nearly constant until the syringe is substantially empty. Moreover, the present invention incorporates features that minimize the possibility of sudden separation of its components, either from each other or from the syringe, due to breakage of the elastomeric element.

Although the preferred embodiments of the invention have been described herein, several variations and modifications will suggest themselves to those skilled in the pertinent arts. For example, the elastomeric actuation means might comprise a pair of elastic straps, each having one end fixed to a unitary grommet and the opposite end fixed to the end cap. Another variation might include a grommet assembly having two separable parts that snap together, rather than being threaded together. Other embodiments might include variations in the configuration of the finger grip and/or in the structure of the latching means in the end cap sleeve. These and other variations and modifications that may suggest themselves are considered to be within the spirit and scope of the present invention, as defined in the claims that follow.

What is claimed is:

1. A device for actuating a syringe having a barrel for containing a supply of fluid, an outlet tip at the proximal end of the barrel, and a plunger slidably disposed within the barrel for movement between a withdrawn position and an inserted position, the plunger having an actuation portion extending distally from the barrel, the device comprising:

grommet means for seating against the proximal end of the barrel around the outlet tip;

plunger engagement means for engaging the actuation portion; and elastomeric actuation means for elastically connecting the grommet means and the plunger engagement means, so that when the grommet means is seated against the proximal end of the barrel and the plunger engagement means is engaging the actuation portion with the plunger in the withdrawn position, the plunger is biased toward the inserted position.

2. The device of claim 1, wherein the plunger engagement means includes an end cap, comprising:

a substantially cylindrical sleeve, having an open proximal end dimensioned to receive the actuation portion; and an end wall at the distal end of the sleeve, having an interior surface that seats against the actuation portion when the actuation portion is received in the sleeve.

3. The device of claim 2, wherein the end wall has an exterior surface, and wherein the end cap further comprises a finger grip fixed to the exterior surface of the end wall.

4. The device of claim 1, wherein the actuation portion includes a flattened member with a peripheral edge, and wherein the plunger engagement means includes latching means for releasably holding the peripheral edge of the flattened member.

5. The device of claim 1, wherein the actuation portion includes guide means for receiving the elastomeric actuation means and for positioning the elastomeric actuation means so as to be spaced from the barrel of the syringe.

6. The device of claim 2, wherein the actuation portion includes a flattened member with a peripheral edge, and wherein the end cap further comprises:

latching means, within the sleeve, for releasably holding the peripheral edge of the actuation portion.

7. The device of claim 6, wherein the sleeve has an interior wall surface, and wherein the latching means comprises a finger extending radially inward from the interior wall surface of the sleeve.

8. The device of claim 1, wherein the elastomeric actuation means comprises an elastic strap having a first end portion, a second end portion, and an intermediate portion between the first and second end portions, the first and second end portions being attached to the grommet means, and the plunger engagement means being attached to the intermediate portion.

9. The device of claim 8, wherein the grommet means comprises first and second grommet members that are removably attachable to one another so as to hold the first and second end portions of the elastic strap between them.

10. The device of claim of claim 9, wherein the first end portion of the elastic strap has a first hole therein and the second end portion of the elastic strap has a second hole therein, and wherein the grommet means comprises:

a hollow, substantially cylindrical, externally-threaded fitting dimensioned to fit through the first and second holes, and having an axial bore and an enlarged diameter head with a central orifice aligned with and communicating with the axial bore, the axial bore and the central orifice being dimensioned to receive therethrough the outlet tip of the syringe; and an internally-threaded annular collar that removably threads onto the fitting so as to hold the first and second end portions of the elastic strap against the head of the fitting.

11. The device of claim 10, wherein the second hole is one of a plurality of second holes in a linear array in the second end portion of the elastic strap.

12. The device of claim 8, wherein the plunger engagement means includes an end cap, comprising:
a substantially cylindrical sleeve, having an open proximal end dimensioned to receive the actuation portion;
an end wall at the distal end of the sleeve, having an interior surface that seats against the actuation portion when the actuation portion is received in the sleeve; and
means in the end wall for attachment of the end cap to the intermediate portion of the strap.

13. The device of claim 12, wherein the end wall includes a peripheral flange, and wherein the means in the end wall comprises first and second diametrically-opposed slots in the flange dimensioned for the passage of the strap therethrough.

14. The device of claim 1, wherein the elastomeric actuation means comprises a continuous elastic band removably secured to the grommet means and to the plunger engagement means.

15. The device of claim 14, wherein the plunger engagement means includes an end cap, comprising:
a substantially cylindrical sleeve, having an open proximal end dimensioned to receive the actuation portion;
an end wall at the distal end of the sleeve, having an interior surface that seats against the actuation portion when the actuation portion is received in the sleeve; and
means fixed to the end wall for securing the band to the end cap.

16. The device of claim 15, wherein the means for securing includes first and second diametrically-opposed pairs of guide fingers extending radially from the end wall, each pair of guide fingers being configured and mutually spaced so as to receive the band between the fingers of each pair.

17. A device for actuating a syringe having a barrel for containing a supply of fluid, an outlet tip at the proximal end of the barrel, and a plunger slidably disposed within the barrel for movement between a withdrawn position and an inserted position, the plunger having an actuation portion extending distally from the barrel, the actuation portion terminating in a flattened member having a peripheral edge, the device comprising:
first means for seating against the proximal end of the barrel around the outlet tip;
second means for receiving the actuation portion and seating against the flattened member;
third means, within the second means, for releasably holding the peripheral edge of the flattened member; and
elastomeric actuation means for elastically connecting the first means and the second means, so that when the first means is seated against the proximal end of the barrel and the second means is seated against the flattened member with the plunger in the withdrawn position, the plunger is biased toward the inserted position.

18. The device of claim 17, wherein the second means comprises:
a substantially cylindrical sleeve, having an open proximal end dimensioned to receive the actuation portion; and
an end wall at the distal end of the sleeve, having an interior surface that seats against the flattened member when the actuation portion is received in the sleeve.

19. The device of claim 18, wherein the end wall has an exterior surface, and wherein the second means further comprises a finger grip fixed to the exterior surface of the end wall.

20. The device of claim 18, wherein the sleeve has an interior wall surface, and wherein the third means comprises a finger extending radially inward from the interior wall surface of the sleeve.

21. The device of claim 17, wherein the elastomeric actuation means comprises an elastic strap having a first end portion, a second end portion, and an intermediate portion between the first and second end portions, the first and second end portions being attached to the first means, and the second means being attached to the intermediate portion.

22. The device of claim 21, wherein the second means comprises:
a substantially cylindrical sleeve, having an open proximal end dimensioned to receive the actuation portion;
an end wall at the distal end of the sleeve, having an interior surface that seats against the flattened member when the actuation portion is received in the sleeve; and
fourth means in the end wall for attachment of the second means to the intermediate portion of the strap.

23. The device of claim 22, wherein the end wall includes a peripheral flange, and wherein the means in the end wall comprises first and second diametrically-opposed slots in the flange dimensioned for the passage of the strap therethrough.

24. The device of claim 21, wherein the first means comprises first and second grommet members that are removably attachable to one another so as to hold the first and second end portions of the elastic strap between them.

25. The device of claim of claim 24, wherein the first end portion of the elastic strap has a first hole therein and the second end portion of the elastic strap has a second hole therein, and wherein the first means comprises:
a hollow, substantially cylindrical, externally-threaded fitting dimensioned to fit through the first and second holes, and having an axial bore and an enlarged diameter head with a central orifice aligned with and communicating with the axial bore, the axial bore and the central orifice being dimensioned to receive therethrough the outlet tip of the syringe; and
an internally-threaded annular collar that removably threads onto the fitting so as to hold the first and second end portions of the elastic strap against the head of the fitting.

26. The device of claim 25, wherein the second hole is one of a plurality of second holes in a linear array in the second end portion of the elastic strap.

27. The device of claim 17, wherein the elastomeric actuation means comprises a continuous elastic band removably secured to the first means and to the second means.

28. The device of claim 27, wherein the second means comprises:
    a substantially cylindrical sleeve, having an open proximal end dimensioned to receive the actuation portion;
    an end wall at the distal end of the sleeve, having an interior surface that seats against the flattened member when the actuation portion is received in the sleeve; and
    means fixed to the end wall for securing the band to the second means.

29. The device of claim 28, wherein the means for securing includes first and second diametrically-opposed pairs of guide fingers extending radially from the end wall, each pair of guide fingers being configured and mutually spaced so as to receive the band between the fingers of each pair.

30. A device for actuating a syringe having a barrel for containing a supply of fluid, an outlet tip at the proximal end of the barrel, and a plunger slidably disposed within the barrel for movement between a withdrawn position and an inserted position, the plunger having an actuation portion extending distally from the barrel, the device comprising:
    an elastic strap having first and second end portions and an intermediate portion;
    plunger engagement means, attached to the intermediate portion of the strap, for engaging the actuation portion of the plunger; and
    grommet means for attaching the first and second end portions of the strap together, and for seating against the proximal end of the barrel around the outlet tip, so that when the grommet means is seated against the proximal end of the barrel and the plunger engagement means is engaging the actuation portion of the plunger with the plunger in the withdrawn position, the plunger is biased toward the inserted position, the grommet means comprising first and second grommet members that are removably attachable to each other and to the strap near the first and second end portions thereof.

31. The device of claim 30, wherein the strap includes length adjustment means for selectively changing the position near the second end portion of the strap at which the first and second grommet members are attached.

32. The device of claim 31, wherein the length adjustment means includes a plurality of holes in a linear array near the second end portion of the strap.

33. The device of claim 32, wherein the strap has a first hole near the first end portion;
    wherein the first grommet member comprises a hollow, substantially cylindrical, externally-threaded fitting dimensioned to fit through the first hole and a selected one of the plurality of holes, and having an axial bore and an enlarged diameter head with a central orifice aligned with and communicating with the axial bore, the axial bore and the central orifice being dimensioned to receive therethrough the outlet tip of the syringe; and
    wherein the second grommet member comprises an internally-threaded annular collar that removably threads onto the fitting so as to hold the first and second end portions of the elastic strap against the head of the fitting.

34. The device of claim 30, wherein the plunger engagement means includes an end cap, comprising:
    a substantially cylindrical sleeve, having an open proximal end dimensioned to receive the actuation portion; and
    an end wall at the distal end of the sleeve, having an interior surface that seats against the actuation portion when the actuation portion is received in the sleeve.

35. The device of claim 34, wherein the end wall has an exterior surface, and wherein the end cap further comprises a finger grip fixed to the exterior surface of the end wall.

36. The device of claim 30, wherein the actuation portion includes a flattened member with a peripheral edge, and wherein the plunger engagement means includes latching means for releasably holding the peripheral edge of the flattened member.

37. The device of claim 34, wherein the actuation portion includes a flattened member with a peripheral edge, and wherein the end cap further comprises:
    latching means, within the sleeve, for releasably holding the peripheral edge of the flattened member.

38. The device of claim 37, wherein the sleeve has an interior wall surface, and wherein the latching means comprises a finger extending radially inward from the interior wall surface of the sleeve.

39. A device for actuating a syringe having a barrel for containing a supply of fluid, an outlet tip at the proximal end of the barrel, and a plunger slidably disposed within the barrel for movement between a withdrawn position and an inserted position, the plunger having an actuation portion extending distally from the barrel, the device comprising:
    plunger engagement means for engaging the actuation portion of the plunger;
    grommet means for seating against the proximal end of the barrel around the outlet tip; and
    an elastic band secured between the grommet means and the plunger engagement means;
    whereby, when the grommet means is seated against the proximal end of the barrel and the plunger engagement means is engaging the actuation portion of the plunger with the plunger in the withdrawn position, the plunger is biased toward the inserted position by the elastic band.

40. The device of claim 39, wherein the plunger engagement means comprises:
    a substantially cylindrical sleeve, having an open proximal end dimensioned to receive the actuation portion;
    an end wall at the distal end of the sleeve, having an interior surface that seats against the actuation portion when the actuation portion is received in the sleeve; and
    means fixed to the end wall for securing the band to the plunger engagement means.

41. The device of claim 40, wherein the means for securing includes first and second diametrically-opposed pairs of guide fingers extending radially from the end wall, each pair of guide fingers being configured and mutually spaced so as to receive the band between the fingers of each pair.

* * * * *